(12) United States Patent
Chang et al.

(10) Patent No.: US 9,353,235 B1
(45) Date of Patent: May 31, 2016

(54) MEDICAL DEVICE WITH POROUS SURFACE AND METHOD FOR PRODUCING SAME

(71) Applicant: Vertera, Inc., Atlanta, GA (US)

(72) Inventors: Wei-Hsiang Chang, Duluth, GA (US); Stephen Lee Laffoon, Atlanta, GA (US); Christopher S. D. Lee, Atlanta, GA (US); David Lee Safranski, Atlanta, GA (US)

(73) Assignee: VERTERA, INC., Atlanta, GA (US)

( * ) Notice: Subject to any disclaimer, the term of this patent is extended or adjusted under 35 U.S.C. 154(b) by 0 days.

(21) Appl. No.: 14/747,660

(22) Filed: Jun. 23, 2015

Related U.S. Application Data

(63) Continuation of application No. 14/587,856, filed on Dec. 31, 2014, now Pat. No. 9,085,665.

(51) Int. Cl.
*B29C 67/20* (2006.01)
*C08J 9/26* (2006.01)
*A61F 2/02* (2006.01)

(52) U.S. Cl.
CPC ... *C08J 9/26* (2013.01); *A61F 2/02* (2013.01); *A61F 2210/0076* (2013.01); *C08J 2361/16* (2013.01)

(58) Field of Classification Search
CPC ................ C08J 2371/00; C08J 2201/0446; B29C 67/20; B29C 67/202
See application file for complete search history.

(56) References Cited

U.S. PATENT DOCUMENTS

| | | | |
|---|---|---|---|
| 699,026 A | 4/1902 | Shaler | |
| 3,679,538 A | 7/1972 | Druin et al. | |
| 4,487,731 A | 12/1984 | Kobayashi | |
| 4,863,604 A | 9/1989 | Lo et al. | |
| 6,183,873 B1 | 2/2001 | Clarke | |
| 7,964,206 B2 | 6/2011 | Suokas et al. | |
| 2004/0026811 A1 | 2/2004 | Murphy et al. | |
| 2004/0138058 A1 | 7/2004 | Sambasivan et al. | |
| 2007/0191962 A1 | 8/2007 | Jones et al. | |

(Continued)

FOREIGN PATENT DOCUMENTS

DE  10054089 C1  7/2002
DE  102006014174 A1  9/2007

(Continued)

OTHER PUBLICATIONS

International Search Report and Written Opinion for International Application No. PCT/US2009/047286 filed Jun. 12, 2009.

(Continued)

*Primary Examiner* — Stella Yi

(74) *Attorney, Agent, or Firm* — Morris Manning & Martin, LLP; Bryan D. Stewart

(57) ABSTRACT

A method for making a polymer with a porous layer from a solid piece of polymer is disclosed. In various embodiments, the method includes heating a surface of a solid piece of polymer to a processing temperature below a melting point of the polymer and holding the processing temperature while displacing a porogen layer through the surface of the polymer to create a matrix layer of the solid polymer body comprising the polymer and the porogen layer. In at least one embodiment, the method also includes removing at least a portion of the layer of porogen from the matrix layer to create a porous layer of the solid piece of polymer.

5 Claims, 11 Drawing Sheets

EXEMPLARY PROCESS

(56) References Cited

U.S. PATENT DOCUMENTS

| | | |
|---|---|---|
| 2007/0275863 A1 | 11/2007 | Whitmarsh |
| 2010/0151114 A1 | 6/2010 | Parrott |
| 2010/0256804 A1 | 10/2010 | Freeman |
| 2012/0077010 A1 | 3/2012 | Manesis et al. |
| 2012/0323339 A1 | 12/2012 | Olalde Graells et al. |
| 2013/0345827 A1 | 12/2013 | Wallick |

FOREIGN PATENT DOCUMENTS

| | | |
|---|---|---|
| EP | 0512401 A2 | 11/1992 |
| EP | 0714869 A2 | 6/1996 |
| EP | 1162047 A1 | 12/2001 |
| FR | 1171658 A | 1/1959 |
| GB | 829811 A | 3/1960 |
| WO | 9964361 A1 | 12/1999 |
| WO | 0268373 A2 | 9/2002 |
| WO | 03024626 A1 | 3/2003 |
| WO | 03074227 A2 | 9/2003 |
| WO | 03080119 A1 | 10/2003 |
| WO | 2004020362 A1 | 3/2004 |
| WO | 2004082333 A1 | 9/2004 |
| WO | 2007090131 A1 | 8/2007 |

OTHER PUBLICATIONS

International Preliminary Search Report on Patentability for International Application No. PCT/US2009/047286 filed Jun. 12, 2009.
International Search Report and Written Opinion for International Application No. PCT/US2013/055656 filed Aug. 20, 2013.
International Search Report and Written Opinion for International Application No. PCT/US2013/055655 filed Aug. 20, 2013.
International Search Report and Written Opinion mailed on Sep. 23, 2015 in related PCT application No. PCT/US2015/038181.

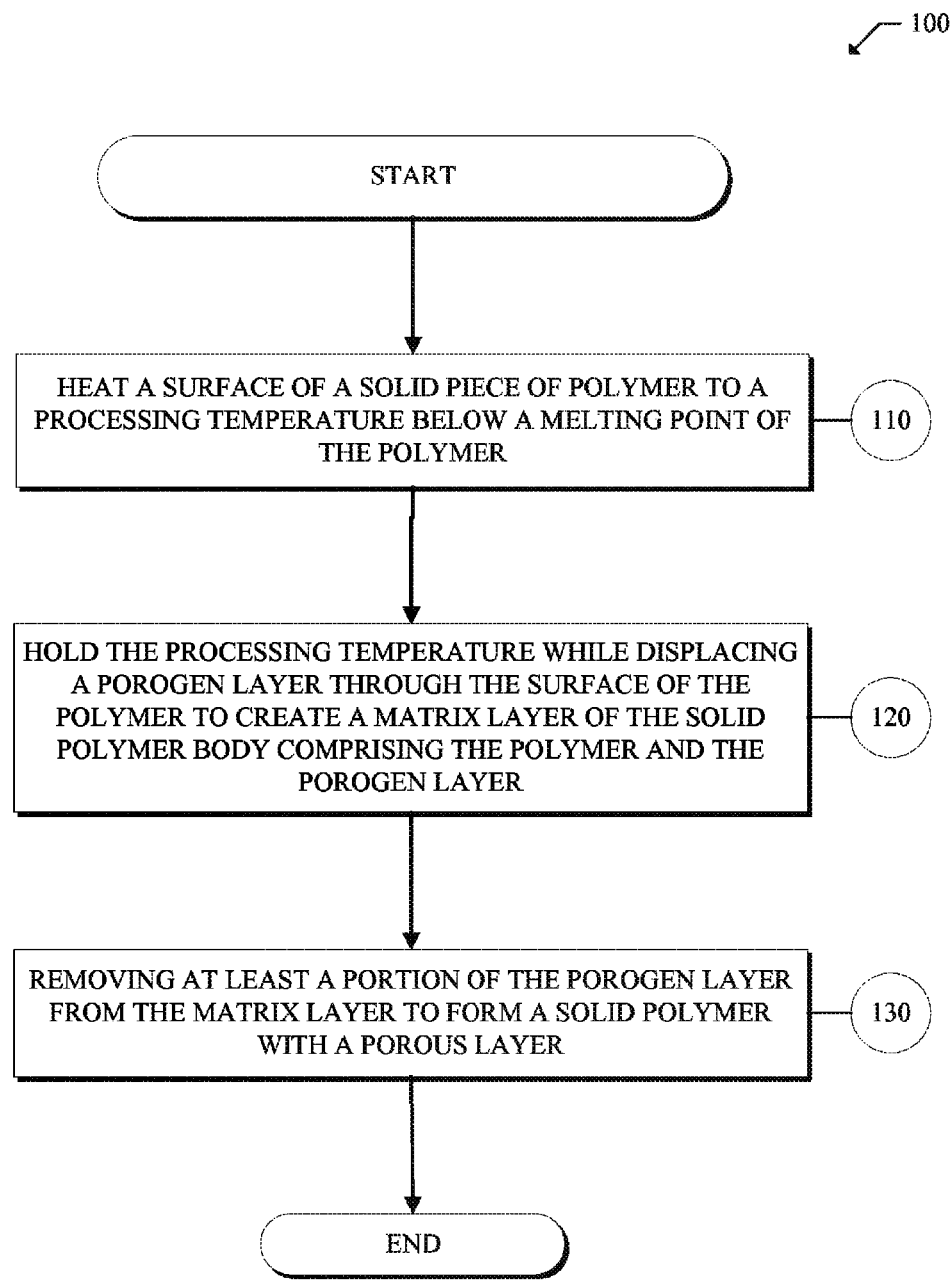
FIG. 1: EXEMPLARY PROCESS

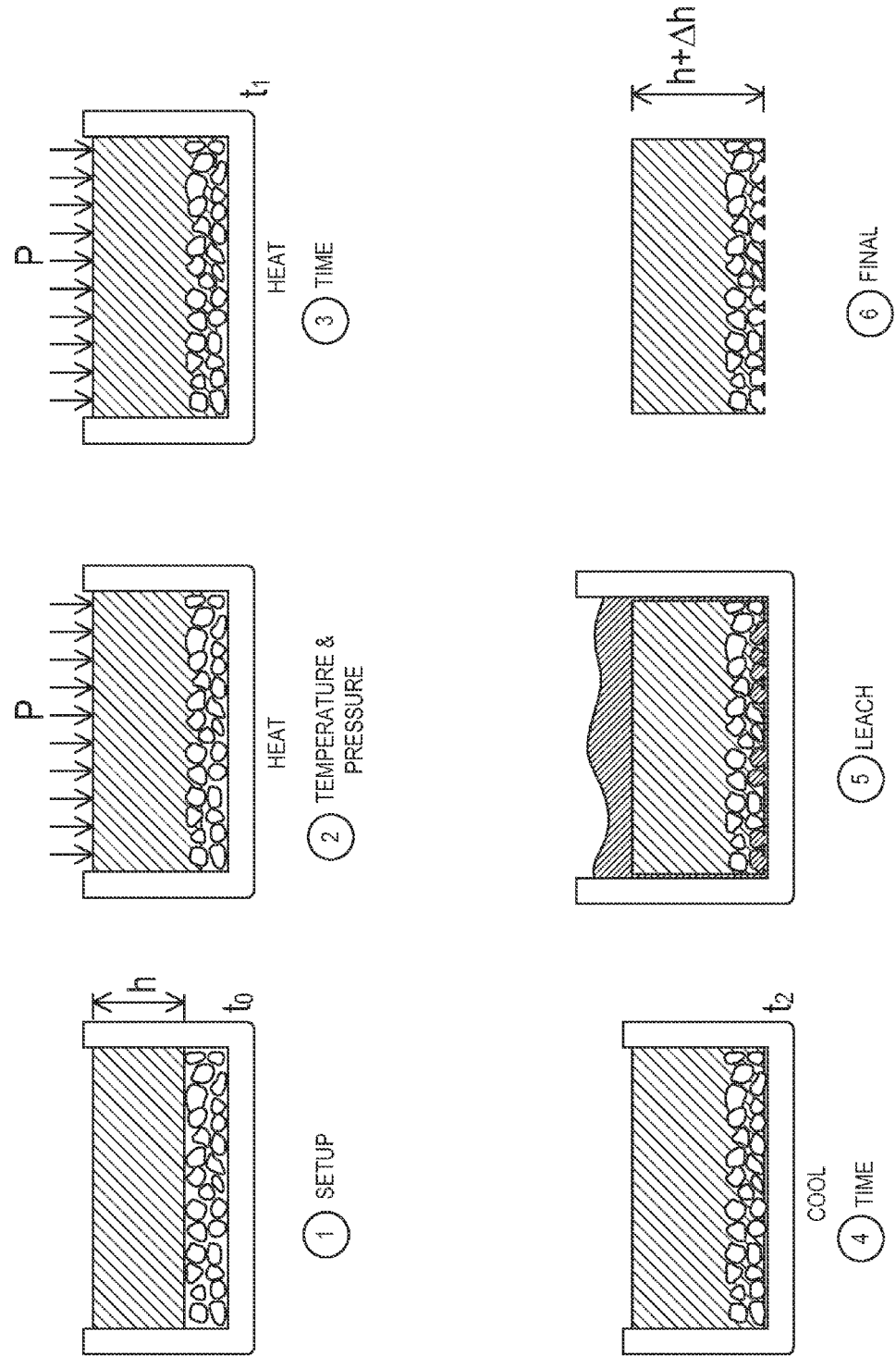
FIG. 2: EXEMPLARY PROCESS

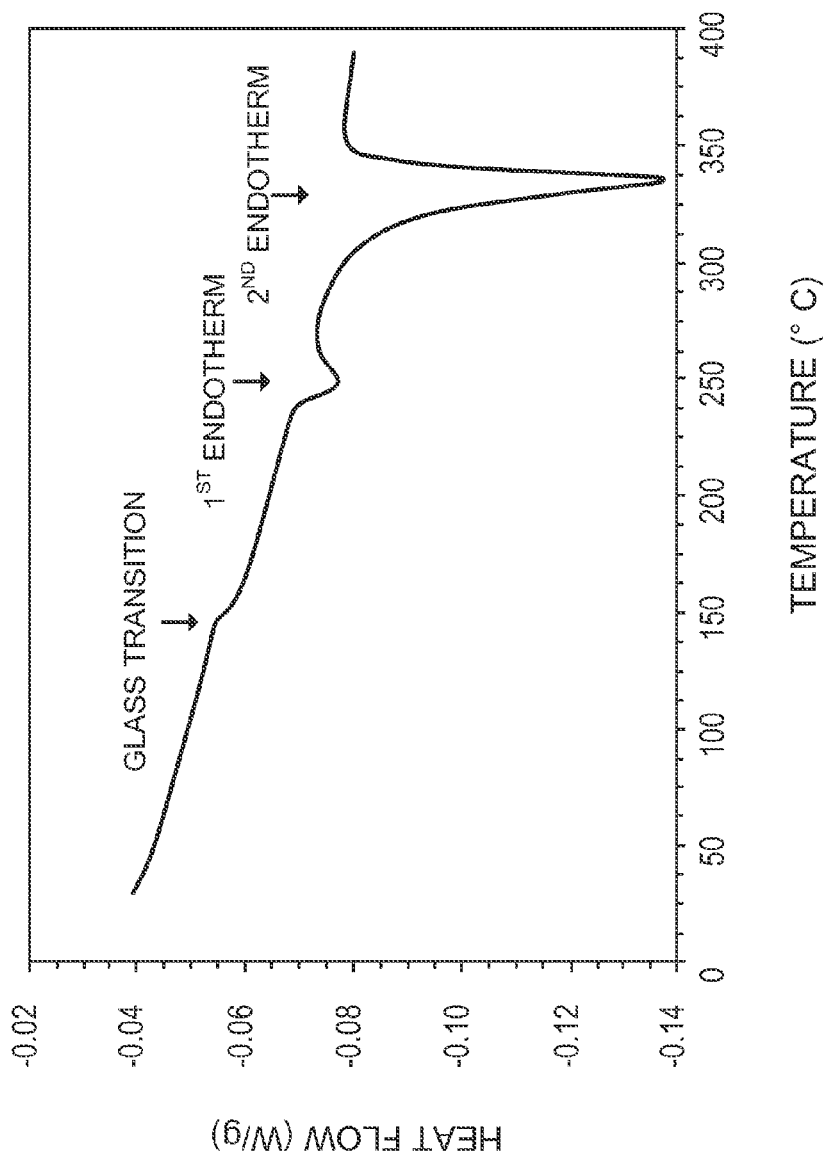
FIG. 3: DIFFERENTIAL SCANNING CALORIMETRY SCAN OF PEEK

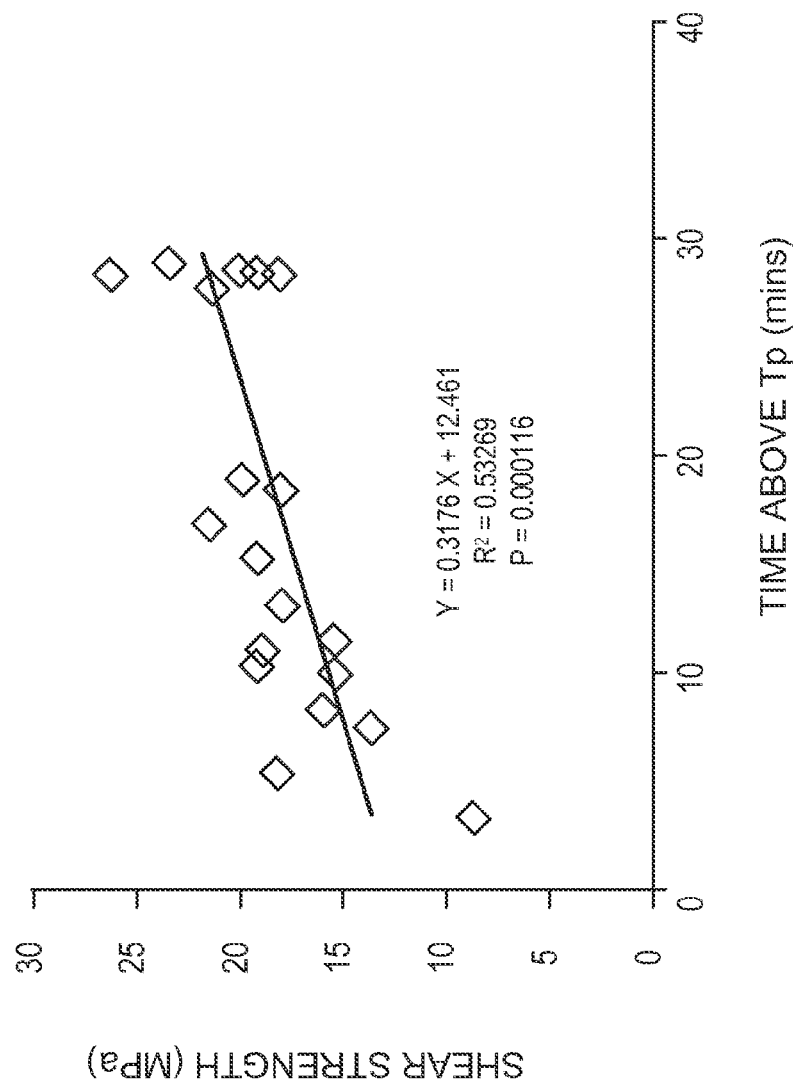
FIG. 4A: EXEMPLARY SHEAR STRENGTH V. TIME PLOT 1

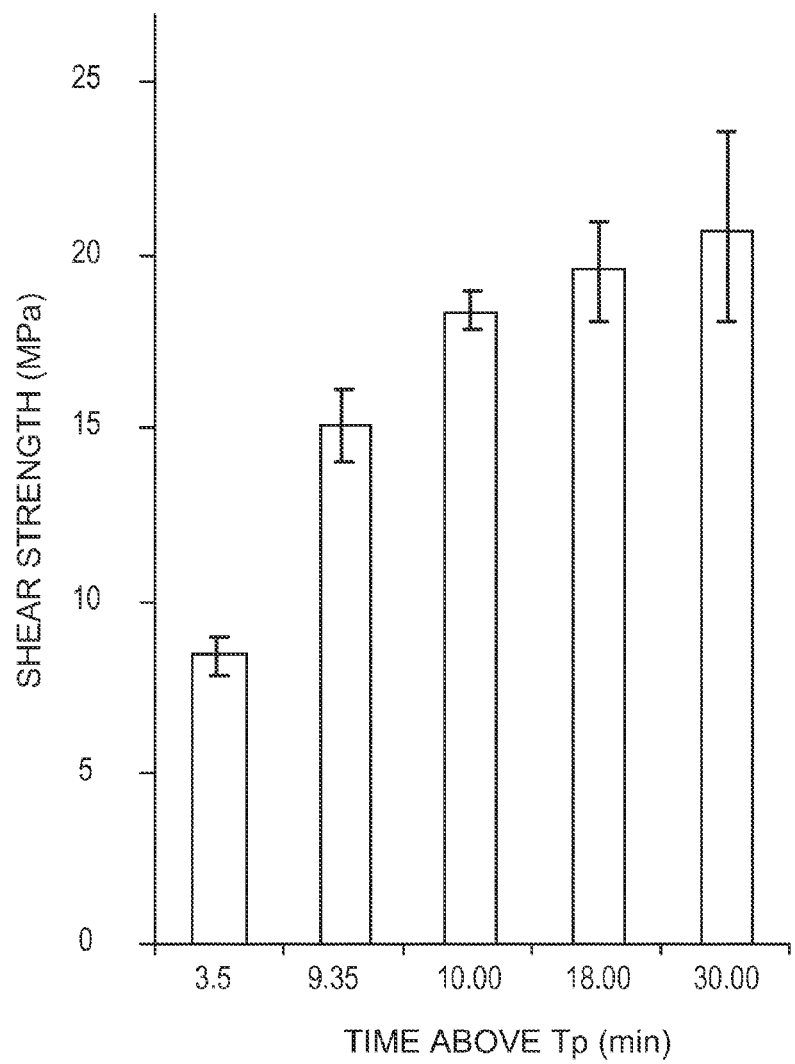
FIG. 4B: *EXEMPLARY SHEAR STRENGTH V. TIME BAR GRAPH 1*

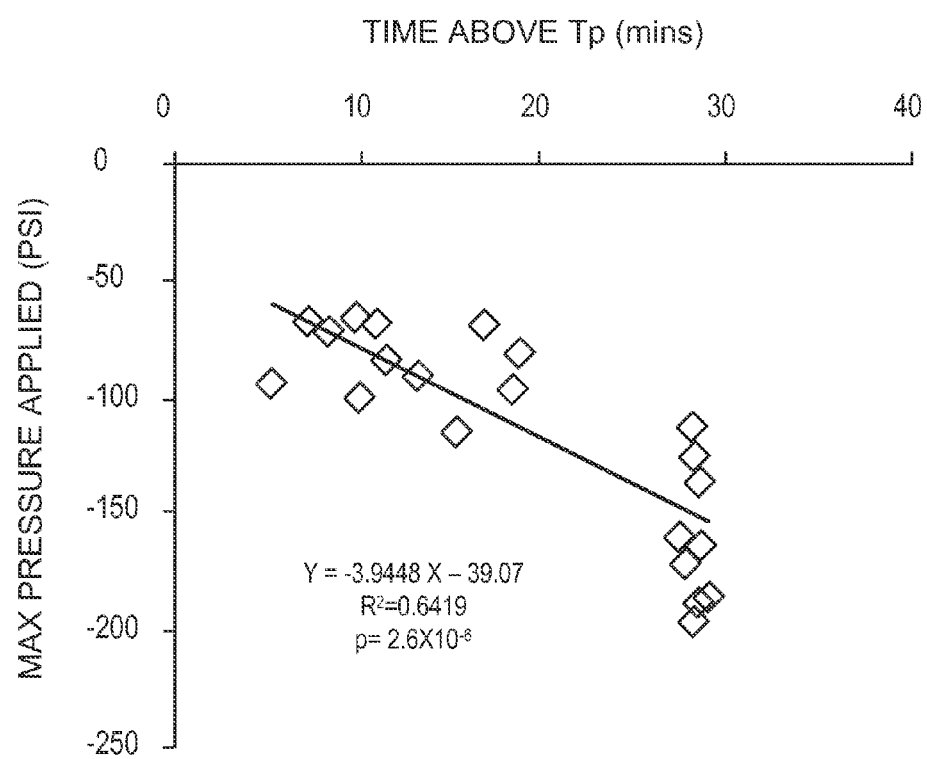
FIG. 4C: *EXEMPLARY MAX FLOW PRESSURE V. TIME PLOT 1*

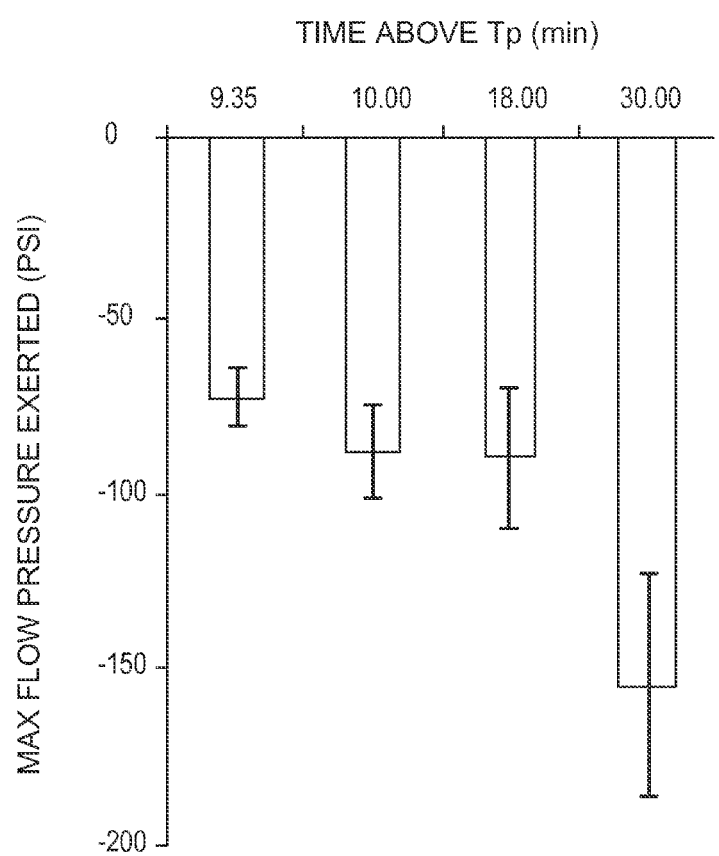
FIG. 4D: EXEMPLARY MAX FLOW PRESSURE V. TIME BAR GRAPH 1

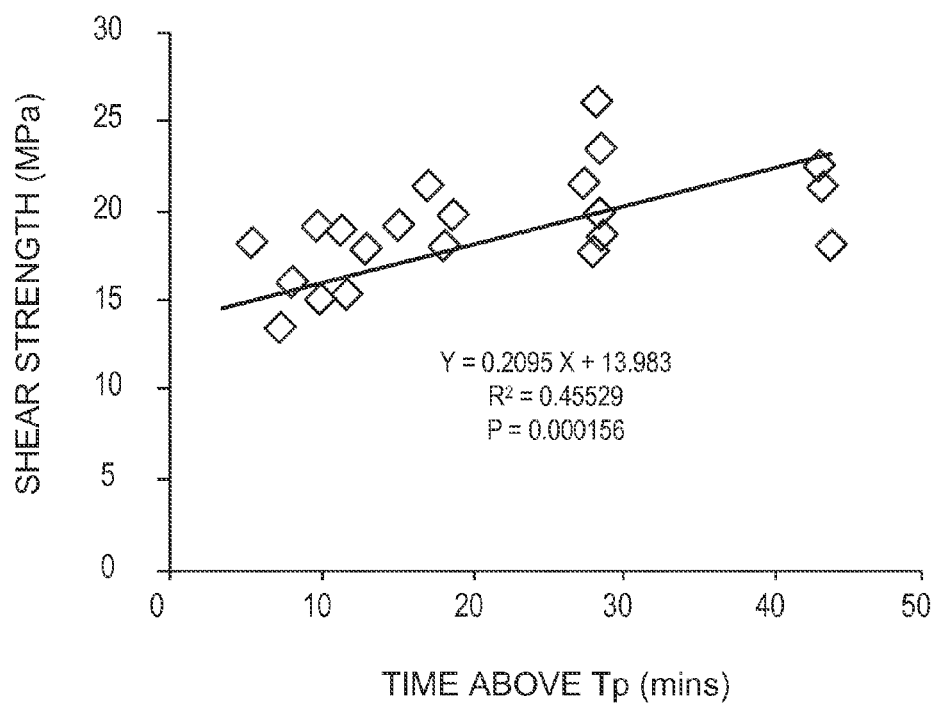
FIG. 5A: *EXEMPLARY SHEAR STRENGTH V. TIME PLOT 2*

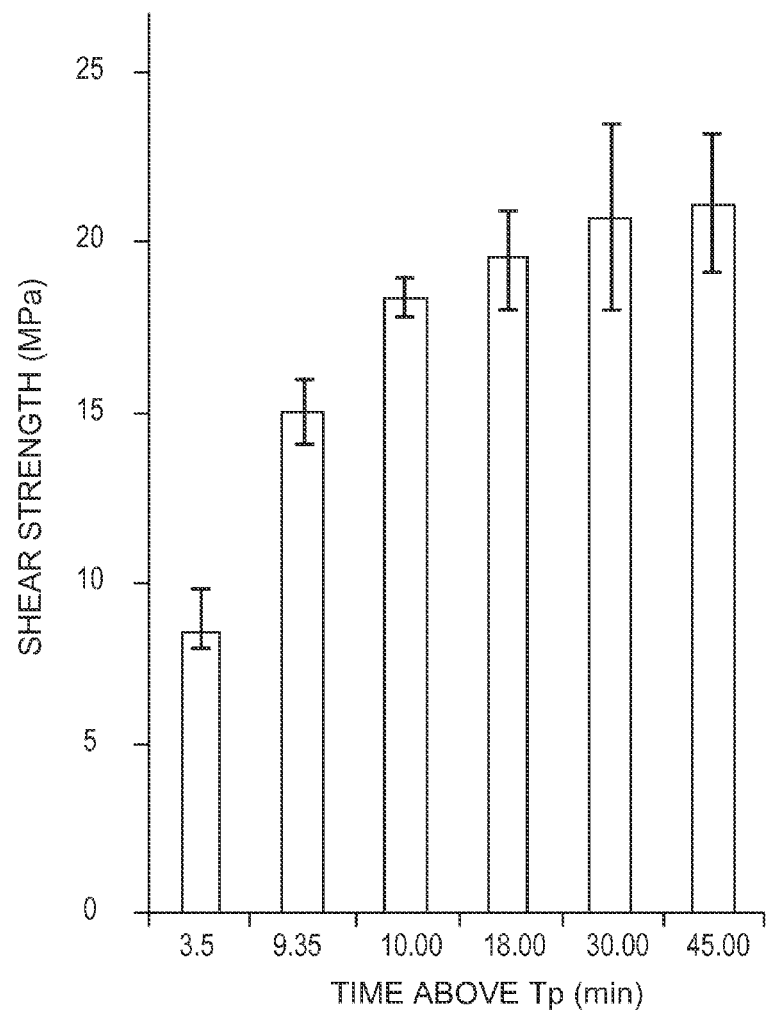
FIG. 5B: *EXEMPLARY SHEAR STRENGTH V. TIME BAR GRAPH 2*

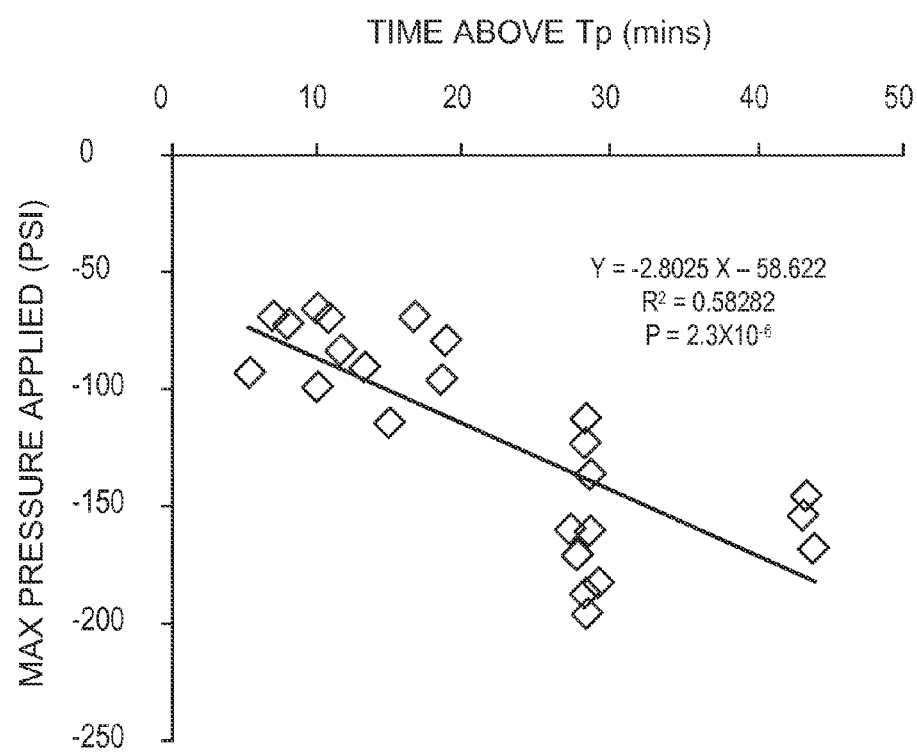
FIG. 5C: *EXEMPLARY MAX FLOW PRESSURE V. TIME PLOT 2*

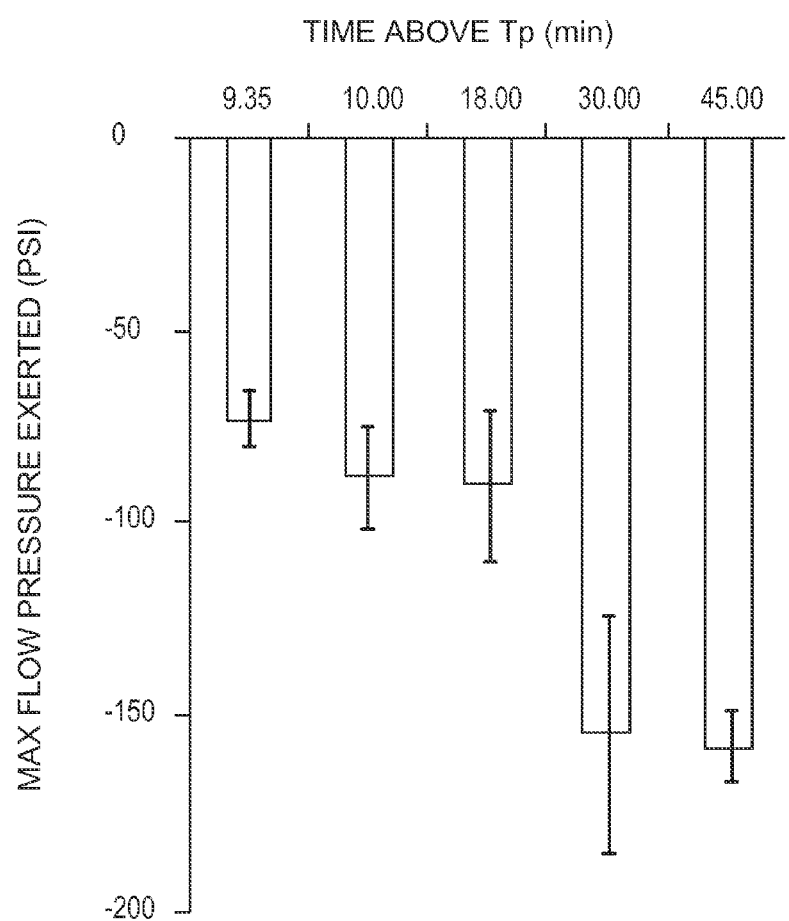
FIG. 5D: *EXEMPLARY MAX FLOW PRESSURE V. TIME BAR GRAPH 2*

MEDICAL DEVICE WITH POROUS SURFACE AND METHOD FOR PRODUCING SAME

CROSS REFERENCE TO RELATED APPLICATIONS

This Application is a continuation application and claims the benefit of and priority under 35 U.S.C. §120 to U.S. patent application Ser. No. 14/587,856, filed Dec. 31, 2014, entitled "Method for Producing Porous Material", by Wei-Hsiang Chang, et al. pending, which is hereby incorporated by reference herein as if set forth herein in its entirety.

TECHNICAL FIELD

The present disclosure relates generally to processes for creating porous polymers.

BACKGROUND

Polymers have been shown to have many advantageous mechanical and chemical properties such as imperviousness to water, low toxicity, chemical and heat resistance, and shape-memory properties. Additionally, polymers are often relatively low cost, easy to manufacture, and versatile in application. These characteristics have led to the use of polymers in many applications such as, for example, medical devices, electronics, optics, computing, and a wide-array of consumer products.

Adding pores to one or more surfaces of a polymer structure may provide further advantages, such as, for example, increasing friction at the one or more porous surfaces and providing better device integration in surgical applications by promoting adjacent tissue in-growth. However, as will be understood by one of ordinary skill in the art, introducing porosity into polymers may, in some instances, weaken desired mechanical properties, such as shear strength at the porous surface. Thus, although introducing pores into such polymers may have certain advantages, it has been limited in application due to a loss in mechanical properties.

BRIEF SUMMARY OF THE DISCLOSURE

One aspect of the present disclosure generally relates to producing a porous surface from a solid piece of polymer. In particular, producing a porous surface from a solid piece of polymer at a processing temperature below a melting point of the polymer to produce a solid piece of polymer with a porous surface integrated into the solid piece of polymer.

In a particular aspect, the present disclosure generally relates to producing a porous surface from a piece of polymer with shear strength that increases substantially linearly with processing time. In some aspects, the present disclosure relates to a method for forming a solid polymer body with pores distributed through at least a portion of the solid polymer body, the method comprising: A) heating a surface of a solid piece of polymer to a processing temperature below a melting point of the polymer; and B) holding the processing temperature while displacing a porogen layer through the surface of the polymer to create a matrix layer of the solid polymer body comprising the polymer and the porogen layer. This particular embodiment may further include a processing temperature that is about one to thirty-eight degrees Celsius less than the melting point of the polymer.

According to various aspects, the present disclosure relates to a method for forming a solid polymer body with pores distributed through at least a portion of the solid polymer body, the method including: A) placing a surface of a solid piece of polyetheretherketone (PEEK) in contact with a portion of a plurality of sodium chloride grain layers; B) heating the surface of the solid piece of PEEK to a processing temperature of about 305 to 342 degrees Celsius; C) holding the processing temperature of the surface of the solid piece of PEEK for a processing period of time of between about twenty and forty minutes to create a viscous layer of PEEK from the solid piece of PEEK; D) displacing at least the portion of the plurality of sodium chloride grain layers through the viscous layer of the solid piece of PEEK, creating a matrix layer of PEEK and sodium chloride grains; and E) leaching one or more of the chloride grains of the plurality of sodium chloride grain layers and cooling the surface of the solid piece of PEEK to form a solid polymer with a porous layer, wherein a shear strength of the porous layer increases substantially linearly with the processing period of time.

Particular aspects of the present disclosure relate to a method including: A) heating a surface of a solid polyetheretherketone (PEEK) body to a maximum processing temperature that is below a melting temperature of the surface of the solid PEEK body by a melting temperature differential; B) displacing a plurality of layers of a porogen through the surface and into a defined distance of the solid PEEK body, creating, thereby, a matrix layer including PEEK and the plurality of layers of the porogen, the matrix layer being integrally connected with the solid PEEK body; C) maintaining throughout the heating and displacing steps, a temperature of the surface of the solid PEEK body that is below the melting temperature by at least the melting temperature differential; and D) removing a portion of the plurality of layers of porogen from the matrix layer, creating, thereby, a porous PEEK layer integrally connected with a remaining portion of the solid PEEK body.

These and other aspects, features, and benefits of the claimed systems and methods will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

FIG. 1 is an exemplary flow chart of an exemplary process for creating a porous polymer, according to one embodiment.

FIG. 2 illustrates an exemplary process for creating a porous polymer, according to one embodiment.

FIG. 3 is an exemplary graph showing results of a differential scanning calorimetry scan of polyetheretherketone (PEEK) showing exemplary endotherms of PEEK under particular conditions, according to one embodiment.

FIG. 4A is an exemplary plot graph showing exemplary shear strength properties of PEEK over time under particular conditions, according to one embodiment.

FIG. 4B is an exemplary bar graph showing exemplary shear strength over time under particular conditions, according to one embodiment.

FIG. 4C is an exemplary plot graph showing exemplary pressure verses time data of PEEK under certain conditions, according to one embodiment.

FIG. 4D is an exemplary bar graph showing exemplary pressure verses time data of PEEK under certain conditions, according to one embodiment.

FIG. 5A is an exemplary plot graph showing exemplary shear strength properties of PEEK over time under particular conditions, according to one embodiment.

FIG. 5B is an exemplary bar graph showing exemplary shear strength properties of PEEK over time under particular conditions, according to one embodiment.

FIG. 5C is an exemplary plot graph showing exemplary pressure verses time data of PEEK under certain conditions, according to one embodiment.

FIG. 5D is an exemplary bar graph showing exemplary pressure verses time data of PEEK under certain conditions, according to one embodiment.

DETAILED DESCRIPTION

This application is related to and incorporates by reference herein the following U.S. patent applications:

U.S. patent application Ser. No. 12/997,343, entitled "Material and Method for Producing the Same," filed on Jun. 12, 2009;

U.S. patent application Ser. No. 13/935,478, entitled "Porous Polymer Layer and Methods of Manufacture," filed Jul. 3, 2013.

Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Overview

According to particular embodiments, the systems and methods herein are directed to a process for producing a porous polymer including: 1) heating a surface of a solid piece of polymer to a processing temperature below a melting point of the polymer; 2) holding the processing temperature while displacing a porogen layer through the surface of the polymer to create a matrix layer of the solid polymer body comprising the polymer and the porogen layer; and 3) removing at least a portion of the porogen layer from polymer. In one or more embodiments, the processing temperature is approximately one (1) to 38 degrees below a melting point of a polymer. As will be understood by one of ordinary skill in the art, different polymers may have different melting temperatures and some polymers may exhibit melting properties at more than one temperature.

This process results in interfacial shear strength between the porous layer and solid polymer body that increases with longer processing times that are above a predetermined processing temperature (Tp), but below a melting point of the polymer. Further, pressure applied to exert polymer flow of polyetheretherketone (PEEK) at a constant rate is significantly correlated statistically (i.e. p-value less than 0.05 as calculated by linear regression analysis) with processing time above a defined processing temperature of 330 degrees Celsius for up to 30 to 45 minutes. This correlation is counter to expected results and indicates that polymer flow viscosity increases with increased processing time below PEEK's melting point of 343 degrees Celsius (e.g., increased processing time at about one to 13 degrees below 343 degrees Celsius, or between about 330 and 342 degrees Celsius).

As will be understood by one of ordinary skill in the art, "polymer flow" or "polymer flow viscosity", as used herein may refer to any flow of a particular polymer and may not necessarily mean flow of a polymer above a melting point of the particular polymer. In specific embodiments, "polymer flow" and "polymer flow viscosity" refer to flow of a polymer below a melting point of the polymer. Alternately, polymer flow or polymer flow viscosity may be referred to as "polymer resistance to displacement" or the like.

As will be understood by one of ordinary skill in the art, any suitable materials may be used in the above process. In at least one embodiment, the polymer in the above exemplary process is polyetheretherketone (PEEK). In one or more embodiments, the porogen in the above exemplary process is sodium chloride grains arranged in one or more layers, such that when the polymer is heated it at least partially flows between the gaps of the layers of the sodium chloride particles.

Exemplary Process

Turning now to FIG. 1, an exemplary process for producing a porous polymer is shown. This exemplary process begins at step 110 by heating a surface of a solid piece of polymer to a processing temperature below a melting point of the polymer. In various embodiments, the surface is heated in any suitable way, such as by conductive heating, microwave heating, infrared heating, or any other suitable heating method.

Any surface of the solid piece of polymer may be heated. In a particular embodiment shown in FIG. 2, a bottom surface is placed in contact with a porogen layer and heated such that the porogen layer is at least partially displaced within the bottom surface. In various embodiments, a top or side surface is placed in contact with a porogen layer and/or heated such that the porogen layer is at least partially displaced within the top or side surface. As will be understood by one of ordinary skill in the art, a "surface" of the solid piece of polymer may be any suitable portion (or all surfaces) of the solid piece of polymer and, in at least one embodiment, is the entire piece of polymer.

The solid piece of polymer may be any suitable material. In a particular embodiment, the polymer is polyetheretherketone (PEEK). In various embodiments, the polymer is any other suitable thermoplastic with similar properties as PEEK, such as any polymer with multiple endotherms and/or broad endotherms and/or any polymer that exhibits flow above the glass transition. The polymer may be, for example, carbon fiber reinforced PEEK, polymethylmethacrylate (PMMA), polycarbonate (PC), polyphenylsulfone (PPSU), polyphenylenesulfide (PPS), polyethersulfone (PES), polyparaphenylene (also known as self-reinforcing polyphenylene or SRP), or thermoplastic polyurethane (TPU).

The processing temperature may be any suitable temperature and may depend upon the melting point for the particular polymer. In a particular embodiment, the polymer is PEEK, with a melting point of about 343 degrees Celsius. In these embodiments (and others), the processing temperature may be any suitable range below the melting point of PEEK (e.g., 343 degrees Celsius). In one or more embodiments, as discussed below, the processing temperature is about one (1) to 38 degrees below the melting point of PEEK (e.g., the processing temperature is approximately 305 to 342 degrees Celsius). In at least one embodiment, the processing temperature is about 330 degrees Celsius for PEEK. In another embodiment, the processing temperature is about 340 degrees Celsius for PEEK. As will be understood by one of ordinary skill in the art, the processing temperature, in particular embodiments, is the processing temperature of the polymer surface.

At step 120, the process continues with holding the processing temperature while displacing a porogen layer through the surface of the polymer to create a matrix layer of the solid polymer body including the polymer and the porogen layer. In various embodiments, the porogen layer includes particles of one or more particular materials such as sodium chloride grains or other salts, sugars, polymers, metals, etc.

The particles of the porogen layer may be arranged in any suitable way. In various embodiments, the particles of the porogen layer are arranged in a regular lattice pattern, with each particle touching at least one other particle. In some embodiments, the particles of the porogen layer are arranged in an irregular geometric pattern and/or are packet down without a planned geometric pattern.

Further, the particles of the porogen layer may be of any suitable size and shape. In particular embodiments, the particles of the porogen layer may be pre-processed such that they are one or more specific shapes, such as substantially spherical, substantially cubic, etc. In at least one embodiment the particles of the porogen layer are packed, irregular grains of a salt.

In various embodiments, the porogen layer is displaced through the surface of the polymer by holding the processing temperature by applying pressure to the polymer to force the polymer (which may be viscous from heating, as discussed herein) through gaps between the porogen layer (e.g., the porogen is packed and arranged such that there are gaps between the particles). In at least one embodiment, the result is a matrix layer with polymer in gaps between the particles of the porogen layer.

In embodiments where the porogen layer is located at a side surface or more than one surface of the piece of polymer, pressure may be applied in one or more directions to the solid piece of polymer. In one or more such embodiments, pressure may be applied to all sides of the solid piece of polymer (e.g., to create a structure with more than one porous surface).

The porogen layer may be displaced through the surface of the polymer to any suitable depth. In a particular embodiment, the porogen layer is displaced through the surface of the polymer to a depth of approximately 0.2 mm to 2.0 mm.

At step 130, the process continues with removing at least a portion of the porogen layer from the matrix layer to form a solid polymer with a porous layer. As will be understood by one of ordinary skill in the art, the portion of the porogen layer to be removed may be removed in any suitable way and the method of removal may be dependent upon the composition of the porogen layer. Exemplary methods of removing all or a portion of the porogen layer include (but are not limited to): leaching, washing, etching, vaporizing, volatilizing, etc. For example, in embodiments where the porogen layer includes sodium chloride grains, some or all of the sodium chloride grains may be removed by leaching (e.g., dissolving all or a portion of the porogen layer with a particular solvent).

As will be understood by one of ordinary skill in the art, any portion of the porogen layer may be removed. In various embodiments, the desired final product may include a solid polymer portion, a matrix layer, and a porous layer. In these embodiments, only a portion of the porous layer may be removed (e.g., to a certain depth), leaving a structure including a solid polymer layer, a matrix layer (including the polymer and porogen) and a porous polymer layer. In some embodiments, the desired structure does not include any of the porogen layer and substantially all of the porogen layer is removed, resulting in a structure that includes a solid polymer and a porous polymer layer. In embodiments where the matrix layer is the desired outcome, this step 130 may be omitted.

FIG. 2 depicts an exemplary process for producing a porous polymer under certain conditions. In particular, FIG. 2 shows a polymer sample placed in contact with a packed array of porogen (sodium chloride) grains at step 1. In this particular example, the porogen grains are arranged at a depth of approximately 0.2 to 2 mm. In various embodiments, the arrangement of porogen grains affects the arrangement of pores in a resulting porous layer of the polymer sample and thus, the depth may be any suitable depth depending on the desired depth of pores or of a resulting matrix layer. For example, porogen grains may be arranged at depths of approximately 0.05 mm to 5 mm or any suitable range in between.

Continuing with step 1, the surface of the polymer in contact with the porogen grains is heated to a particular processing temperature under an initial pressure of about 2 PSI. In various embodiments, the particular processing temperature is below a melting point of the polymer. For example, as discussed below, PEEK exhibits melting temperatures at approximately 240 and 343 degrees Celsius.

As will be understood by one of ordinary skill in the art, the initial pressure may be any suitable initial pressure. In various embodiments, the initial pressure is about 0.1 to 10 PSI. In some embodiments, the initial pressure and the final pressure are the same (e.g., the same pressure is held constant throughout the entire process).

At step 2, once the polymer surface is heated to the processing temperature, additional pressure is applied to the polymer. In particular embodiments, the processing temperature and the additional pressure is held for a predetermined processing time and, as shown in step 3, the porogen is displaced within the surface of the polymer, creating a pore network (e.g., under particular conditions, the polymer flows between the porogen). According to various embodiments, the processing time is for about zero (0) to 45 minutes. In one embodiment, the processing time is for about 30 minutes.

The additional pressure may be any suitable pressure. In particular embodiments the additional pressure is up to 250 PSI. In one or more embodiments, the additional pressure is between 50 and 250 PSI. In at least one embodiment, the additional pressure is about 150 PSI.

At step 4, the additional pressure and heat are removed from the polymer and the polymer surface is cooled in a controlled fashion to manage solidification and crystallization. At step 5, the porogen grains are leached, leaving behind a thin porous surface layer that is integrally connected with the solid polymer body. Precise control of local temperature, pressure, and time may achieve desired pore layer characteristics. As will be understood by one of ordinary skill in the art, as shown in step 6, the introduction of surface porosity may result in expansion of the total polymer structure, indicated by the change in height, $\Delta h$.

Exemplary Data

Exemplary PEEK Data

As will be further discussed herein, PEEK exhibits melting properties at two temperatures under particular conditions. As shown in FIG. 3, PEEK exhibits several thermal transitions in this differential scanning calorimetry (DSC) scan. The first (lowest temperature) transition is the glass transition, which is characterized by a shift in the heat capacity of the polymer. As shown, this glass transition occurs at approximately 145 degrees Celsius.

Continuing with FIG. 3, PEEK displays higher temperature transitions, characteristic of melting (e.g., endotherms).

As will be understood by one of ordinary skill the art, the enthalpy of melting, the increased heat energy required to overcome the crystalline order, is shown by the area of the endotherm. Notably, in the embodiment shown in FIG. 3, PEEK shows a double melting behavior under these conditions with a small (lower temperature) endotherm and a large (higher temperature) endotherm. As shown, the first endotherm is measured at approximately 240 degrees Celsius and the second endotherm is measured at approximately 343 degrees Celsius. This "double peak" behavior has been explained as a two-stage melting process occurring due to varying size crystallites. However, it should be noted that melting occurs over a range of temperatures and the melting temperature (Tm) is generally determined from the temperature corresponding to the peak maximum of the second melting endotherm (e.g., 343 degrees Celsius, shown here). It should also be noted that endotherms for samples of a polymer may vary based on crystallinity of the polymer; thus, samples of the same polymer may have slightly varying endotherms based on slightly different crystalline structures (e.g., one PEEK sample may have a first endotherm at 239.5 degrees Celsius and a second PEEK sample may have a first endotherm at 241 degrees Celsius).

Exemplary Shear Strength Data

FIGS. 4A and 4B, show exemplary shear strength for PEEK measured over processing times of zero (0) to 30 minutes. As shown in FIGS. 4A and 4B, resulting interfacial shear strength between the porous layer and solid polymer body increases with longer processing times above a predetermined processing temperature (Tp). In particular, FIGS. 4A and 4B show that shear strength between the porous layer and solid polymer body increases substantially linearly with increased processing times between zero (0) and 30 minutes at temperatures of Tp. Tp in this instance is 330 degrees Celsius, which, as depicted in FIG. 3 and discussed above, is below the 343 degrees Celsius melting point of PEEK.

FIGS. 5A and 5B show exemplary shear strength for PEEK measured over processing times of about zero (0) to 40 minutes. As shown in FIGS. 5A and 5B, the shear strength of PEEK potentially begins to plateau between a processing time of around 30 to 40 minutes. Particularly, the shear strength of PEEK is significantly correlated statistically (i.e. p-value less than 0.05 as calculated by linear regression analysis) with processing time above a defined processing temperature of about 330 degrees Celsius (which is thirteen degrees lower than the melting temperature for PEEK of 343 degrees Celsius) for up to about 30 to 45 minutes.

Exemplary Pressure Data

FIGS. 4C and 4D show pressure data verses time above processing temperature (Tp), while holding a constant polymer flow rate (as discussed herein, polymer flow may refer to polymer flow below a melting temperature of the polymer). The polymer flow rate may be any suitable rate, such as approximately two (2) mm/minute. As will be understood by one of ordinary skill in the art, FIGS. 4C and 4D (and 5C and 5D) depict pressures trending in a negative direction, which indicates an increase in pressure acting in compression. It should be understood that an increase in pressure may be shown as positive or negative.

FIGS. 4C and 4D provide a potential explanation for the substantially linear increase in shear strength with increased processing time above a specified processing temperature as shown in FIGS. 4A and 4B (about 330 degrees Celsius in this instance, which is below the 343 degrees Celsius melting temperature of PEEK). In particular, the increased shear strength may be due to an increase in polymer flow viscosity. As will be understood by one of ordinary skill in the art, polymer flow viscosity typically decreases or remains constant as it is heated for longer periods of time. However, as shown in FIGS. 4C and 4D, pressure applied to exert polymer flow at a constant rate is significantly correlated statistically (i.e. p-value less than 0.05 as calculated by linear regression analysis) with processing time above a defined processing temperature of about 330 degrees Celsius for up to 30 to 45 minutes. This correlation is counter to expected results and indicates that polymer flow viscosity increases with processing time below 343 degrees Celsius. This phenomenon appears to plateau around 30 to 45 minutes as shown in FIGS. 5C and 5D.

As will be understood by one of ordinary skill in the art, FIGS. 4C, 4D, 5C, and 5D show data based on holding a constant rate of polymer flow (e.g., polymer flow is held constant and pressure applied to hold the polymer flow constant over time is measured), but this process may operate in the reverse. In various embodiments, pressure is known and applied linearly to keep polymer flow constant.

Exemplary Use Cases

Materials created from the processes described herein may have a wide variety of uses. In particular embodiments, the processes described herein may be beneficial in any application where it is desired to adhere a material to the second material with different properties (e.g., adhere a first polymer with a first stiffness to a second polymer with a second stiffness). Such as, for example, adhering a soft polymer (e.g., polyethylene, polyvinyl-alcohol, or polycarbonate-urethane) to a harder polymer such as PEEK. This example may be applicable for knee or hip replacements. As a second example, porous polymers may be used in medical devices and more particularly for orthopedic applications to promote tissue ingrowth. Other exemplary uses may be aerospace, automotive, and other fields.

CONCLUSION

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope.

What is claimed is:

1. A method comprising the steps of:
   heating a surface of a solid polyetheretherketone (PEEK) body to a maximum processing temperature that is below a melting temperature of the surface of the solid PEEK body by a melting temperature differential;
   displacing a plurality of layers of a porogen through the surface and into a defined distance of the solid PEEK body, creating, thereby, a matrix layer including PEEK and the plurality of layers of the porogen, the matrix layer being integrally connected with the solid PEEK body;
   maintaining throughout the heating and displacing steps, a temperature of the surface of the solid PEEK body that is below the melting temperature by at least the melting temperature differential; and removing a portion of the plurality of layers of porogen from the matrix layer, creating, thereby, a porous PEEK layer integrally connected with a remaining portion of the solid PEEK body, wherein the melting temperature differential is between one degree Celsius and thirty-eight degrees Celsius.

2. The method of claim 1, wherein the melting temperature differential is about eight degrees Celsius.

3. The method of claim 1, further comprising wherein the heating step is for a preselected period of time before the displacing step.

4. The method of claim 3, wherein the preselected period of time is between twenty and forty minutes.

5. The method of claim 3, wherein the preselected period of time is less than thirty minutes.

\* \* \* \* \*